United States Patent [19]

Chen

[11] Patent Number: 5,033,720
[45] Date of Patent: Jul. 23, 1991

[54] APPARATUS FOR DETERMINING METAL PROPERTIES

[75] Inventor: Hong-Bin Chen, Kaohsiung, Taiwan

[73] Assignee: China Steel Corporation, Taiwan

[21] Appl. No.: 499,198

[22] Filed: Mar. 23, 1990

Related U.S. Application Data

[63] Continuation of Ser. No. 212,520, Jun. 28, 1988, abandoned.

[51] Int. Cl.$^5$ .............................................. C21B 7/24
[52] U.S. Cl. ....................................... 266/79; 266/80; 266/99
[58] Field of Search .................. 148/128, 129; 266/88, 266/79, 80, 99, 78

[56] References Cited

U.S. PATENT DOCUMENTS

| | | | |
|---|---|---|---|
| 4,407,682 | 10/1983 | Sawa et al. | 148/128 |
| 4,595,427 | 6/1986 | Drew et al. | 266/78 |
| 4,648,916 | 3/1987 | Morita et al. | 148/128 |

Primary Examiner—S. Kastler
Attorney, Agent, or Firm—Ladas & Parry

[57] ABSTRACT

A torsion pendulum apparatus and a dialometer are combined for simultaneous measurement of the internal friction and the expansion of an alloy. The combination is controlled by a programmable controller so as to conduct in-situ measurements of the internal friction and the expansion of a metal during its phase transformation or specific heat treatment. The results of the internal friction measurement and the expansion measurement can be checked and assumed by one another so that more accurate and detailed information can be obtained for the study of metal alloys.

2 Claims, 3 Drawing Sheets

APPARATUS FOR DETERMINING METAL PROPERTIES

This application is a continuation of application Ser. No. 212,520, filed June 28, 1988, now abandoned.

BACKGROUND OF THE INVENTION

1. Field of the Invention

This invention relates to an apparatus for determing the properties of metals an apparatus which measures the internal friction behavior of an alloy during its phase transformation.

2. Description of the Prior Art

The measuring techniques of internal friction that have been developed in the past few decades, i.e. the torsion pendulum method, the transverse vibration method and others for measuring internal friction behavior of metals, provide significant contributions to the study of metals. The techniques of measuring internal friction are used to measure the situations of solid solutions in a metal alloy, such as the solute content of nitrogen and/or of carbon in steel, the distribution and diffusion of some elements in an alloy, and other defects in a metal, etc. Therefore, due to the fact that those new techniques provide meaningful measured results of the inside situation of metals, persons in the art can now understand metals much better than before.

Although internal friction measuring has been widely applied in the study of metals, the measuring condition needs to be improved in at least two aspects. Firstly, during a heat-treatment, such as quenching, tempering, and annealing, metals are treated at several different temperatures which cause the structural change, but the internal friction measuring of the metal specimens has only been conducted after the whole heat treatment procedure has been completed. That is to say, for example, the known skills can't measure the internal friction behavior of the incubation period of a over cooled austenite of the transformations during the heat treatment, but only provides the measured data of heat treated specimens whose phase is in a steady and/or final state. Secondly, due to the limitation of experimental equipment, the known skills can not be performed at high temperatures, such as 750° C. to 1100° C. At these high temperatures known equipment can not measure the in-situ internal friction behavior of a metal specimen during the heat treatment procedure.

SUMMARY OF THE INVENTION

Accordingly, the primary object of the present invention is to provide an apparatus for measuring the internal friction behavior of a metal alloy during the period of alloy phase transformation.

Another object of the present invention is to provide an apparatus for measuring both the internal friction behavior, and the expansion and/or magnetic property variation curve of a metal alloy during a heat treatment procceding so as to confirm whether the measurement is taken in the incubation period or other period of phase transformation of the metal.

Still another object of the present invention is to provide an apparatus for measuring the in-situ internal friction behavior of a metal alloy during a heat treatment proceeding.

Yet another object of the present invention is to provide an apparatus which conducts the measurements of the in-situ internal friction, expansion curve, and magnetic property variation curve of a metal alloy during heat treatment such that internal friction variations, from one phase to another, of the alloy can be clearly measured. In addition, the present apparatus can also perform the same task as the conventional one, that is measuring the internal friction of the heat treated metal alloy whose phase is in a steady state. These and other objects can be achieved by the provision of a combination comprising an internal friction measuring apparatus, a dialometer, a heating and cooling system, and a programmable controller to control the measurements and the heating and cooling system.

The features and characteristics of the present invention will become more obvious from the following detailed description of a preferred embodiment of the invention in conjunction with the drawings.

DETAILED DESCRIPTION OF THE PREFERRED EMBODIMENT

Figure 1:
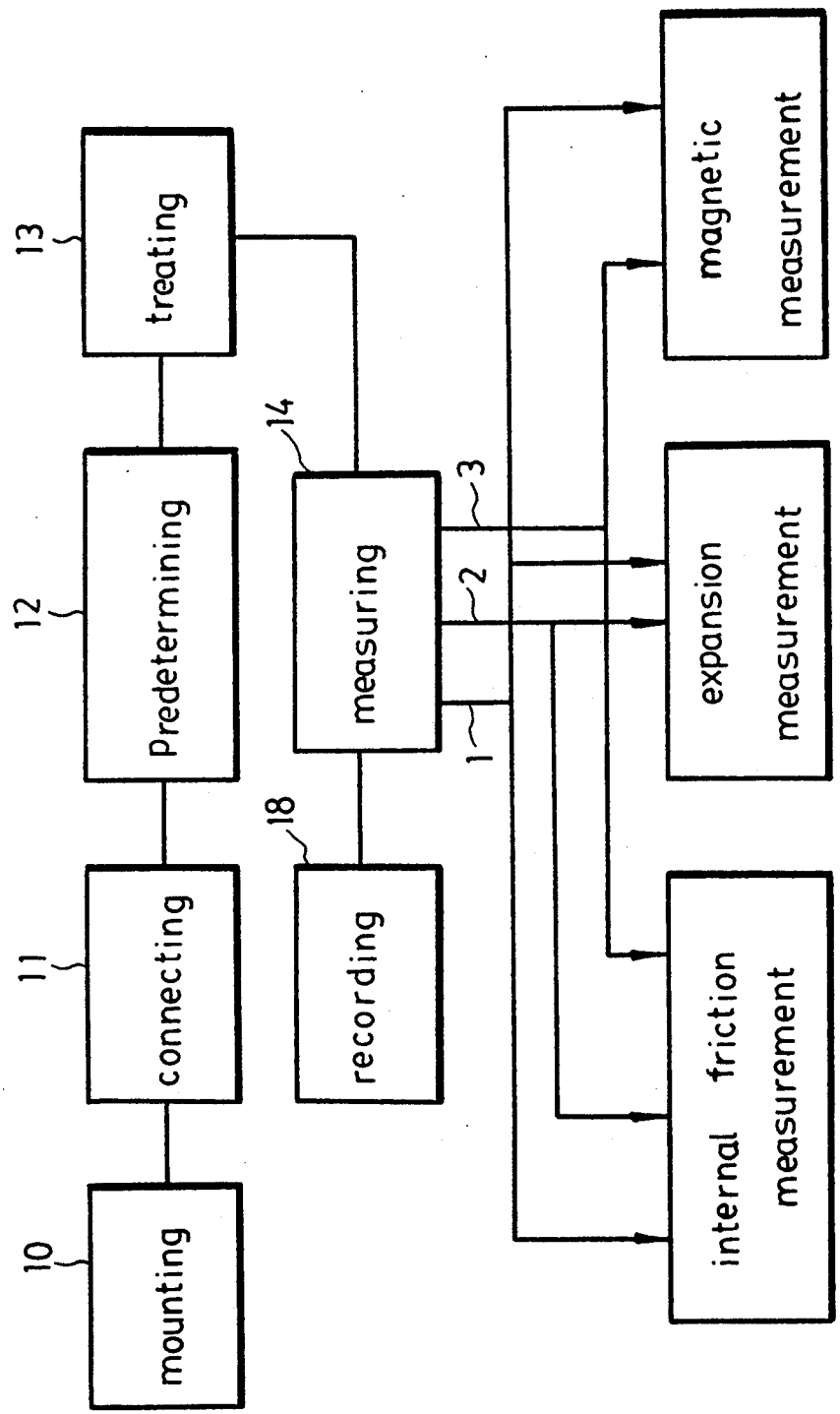
FIG. 1 is a flow-chart of block diagrams for illustrating the steps conducted by the apparatus of this invetion.

In FIG. 1 a flow chart of the steps of measurements that can be conducted by the apparatus of this invention in which numeral 10 indicates a step of mounting a metal specimen on a measuring device; numeral 11 indicates a step of connecting a temperature measuring device, such as a thermal couple, to the metal specimen; numeral 12 indicates a step of predetermining a temperature variation pattern of the specimen by a programmable temperature controller; numeral 13 indicates a step of treating the metal specimen under the control of the temperature controller; numeral 14 indicates a step of measuring the in-situ internal friction behavior, expansion curve and/or magnetic property variation curve of the metal specimen; and numeral 18 indicates a step of recording the measured data so as to provide a better understanding of metals. In the heating step 12, the metal specimen may be heated by several different treatments such as annealing, tempering or quenching. No matter what kind of heat treatment is used, the metal specimen is kept at its original position so that an in-situ measurement can be conducted. In the connecting step 11, the temperature measuring device connected to the metal specimen must not cause any appreciable unexpected external friction to the metal specimen. This is in contrast to the torsion pendulum internal testing apparatus, in which the part of the specimen on which the thermal couple is connected will not experience any torsion, i.e. the place near the torsion center of the metal specimen and the place near the fixed end of the specimen. As a matter of fact, the connection between the thermal couple and the specimen is also one of the characteristics of the invention. The thermal couple, according to the invention, is preferably embedded into the fixed end of the specimen so as to get an accurate measurement, particularly during quenching proceedings. In the measuring step 14 one of three different combinations of measurements can be selected, namely, the measurements of the internal friction, the expansion curve and the magnetic property variation curve indicated by numeral 1; measurements of the internal friction and the expansion curve indicated by numeral 2; or measurements of the internal friction and the magnetic property variation curve indicated by numeral 3.

Figure 2:
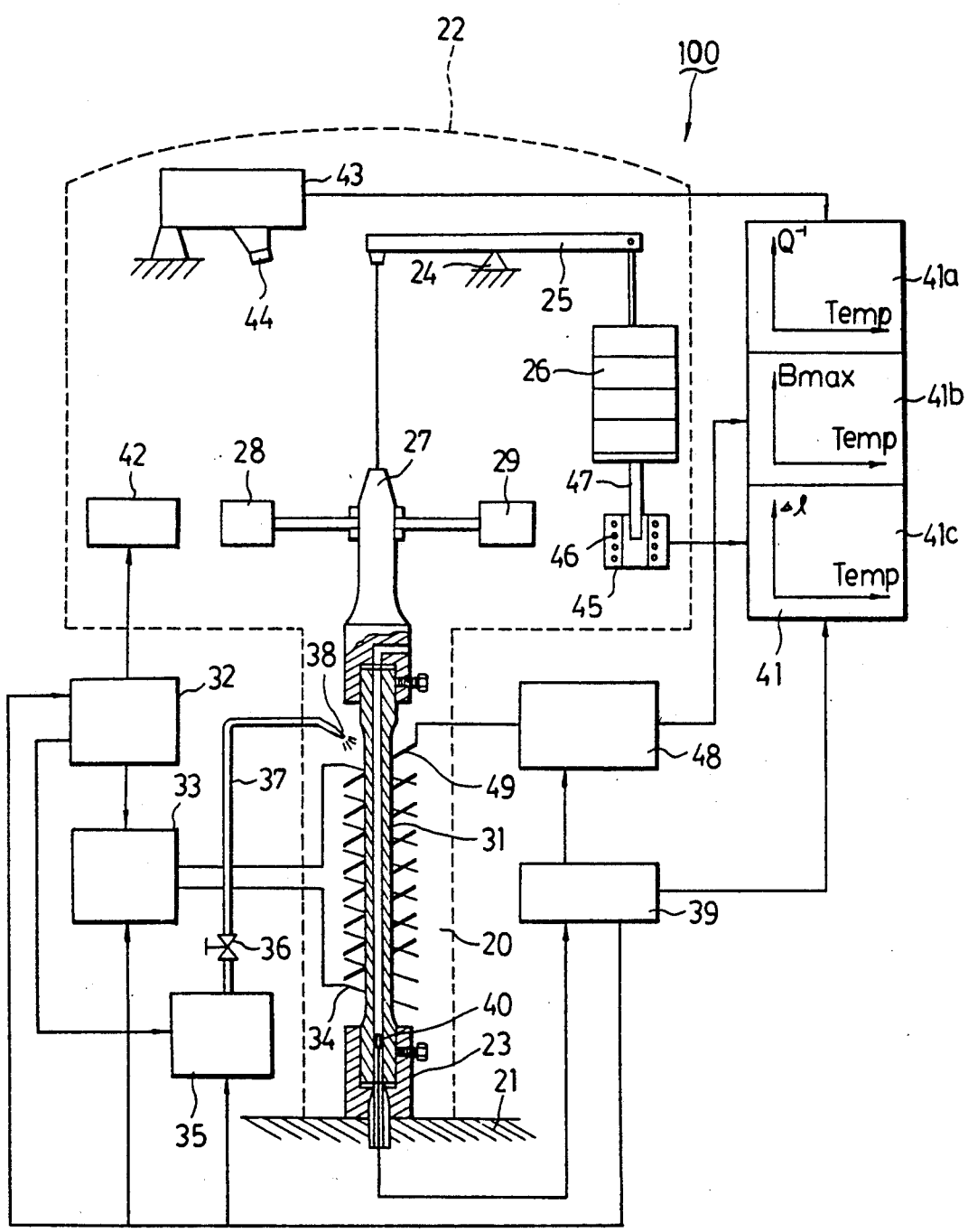
FIG. 2 is a scheme for illustrating an embodiment of the apparatus of this invention.

Turning to FIG. 2, an apparatus 100 of this invention is shown, having a torsion internal friction testing device 20 provided in is a vacuum housing 22 is mounted on a supporting base 21 so that an internal friction measurement can be conducted under the vacuum condition. In the housing 22, a specimen mounting device 23 is provided on the supporting base 21. At the upper portion of the torsion internal friction testing device 20 a lever 25 is fulcrumed at a pointed support 24. A counter balance 26 is connected to end of the lever 25 and a torsion pendulum device 27 is suspended from the other end of the lever 25. A pair of arms 28, 29 are respectively extended from the torsion pendulum device 27 in opposite directions. At the lower portion of the torsion pendulum device 27 there is provided a second specimen mounting device 30 so that a bar-shaped metal specimen 31 can be mounted between the two mounting devices 23 and 30.

The apparatus 100 further comprises a programmable controlling device 32 by which a desirable pattern of measurement can be pre-determined. In other words, with the programmable controlling device 32, a user can select any one of the combinations of the measurements as described above in reference to FIG. 1. Furthermore, the programmable controlling device 32 can also predetermine the conditions of heating, cooling, and isothermal heating in the heat treatment of the metal specimen 31 so as to control the specimen 31 at a desired temperature during the entire measuring proceeding. A heating device 33 is controlled by the programmable controlling device 32 to heat the specimen 31 and can either be an electric heating wire 34 or an induction coil. A cooling device controlled by the programmable controlling device 32 includes a controlliing valve 36, a conduit 37 and nozzle 38. In the cooling operation, using the control valve 36, a cooling gas, such as liquid nitrogen, will be sprayed out of the nozzle 38 onto the heated specimen. A temperature measuring device 39 is connected with a thermal couple 40 whose one end is passed through the mounting device 23 and then embedded into the torsion center of the specimen 31 as clearly shown in FIG. 2. In this way, this connection between the thermal couple 40 and the specimen 31 will not cause an appreciable unexpected external friction to the metal specimen. The measured data of the temperature measuring device 39 will be provided not only to the programmable controlling device 32 but also to a recording device 41.

Preferably, the measurement conducted by the torsion internal friction testing device 20 is conducted under $10^{31\ 2}$ to $10^{-3}$ Torr of vacuum.

A triggering device 42 is provided in the torsion internal friction testing device 20 and controlled by the programmable controlling device 32. The triggering device 42 will cause a torsion to the arms 28, 29 of the torsion pendulum device 27 until it equal to the natural frequency of the torsion pendulum of the metal specimen 31 so as to obtain the desired torsional vibration of the metal specimen 31. In addition, an internal friction measuring device 43 provided with a motion detecting device or photo-detector 44 measures the internal friction values of the metal specimen 31 and sends the measured data to the recording device 41. Therefore, after a heat treatment is applied to the metal specimen 31, a curve 41a showing the internal friction curve of the specimen can be obtained.

Since the damping of the triggered specimen 31 may be fast, some difficulties may be created in proceeding with the measurement. Thus, in accordance with the present invention, it is preferred that when the designed torsional vibration of the triggered specimen 31 is reached, an external energy be applied to make the triggered specimen keep its constant amplitude torisonal vibration. The value of the applied external energy should be the same as the value of the internal friction of the specimen. This novel apparatus of the present invention will render the internal friction measurement more accurate.

In addition, a dilatometer 45 includes a solenoid coil 46 connected with the recording device 41, and a core 47 suspended from the underside of the counter balance 26 and extended into the solenoid coil 46.

Following the variation of temperature during the heat treatment proceeding, the expansion of the specimen 31 will change, making the lever 25 more clockwise or counterclockwise, and making the core 47 move downward or upward. The dilatometer 45 will note the changes in magnetic conductivity which represent corresponding up and down movement of the core 47 and will send the resulting measured data to the recording device 41. Therefore, a curve 41c showing the relation between the variation of temperature and the expansion of the metal specimen will be obtained by the recording device 41.

The apparatus 100 according to this invention further comprises a magnetic detecting device 48 having induction coils 49 surrounding the metal specimen 31. Following the variation of temperature, the induction coils 49 will induce changes in the magnetic flux of specimen 31 and will send the data concerning these changes to the recording device 41. Therefore, a curve 41b showing the relation between the variation of temperature and the magnetic property of the specimen 31 can be obtained.

From the above described apparatus, it should be appreciated that due to the application of the programmable controlling device 32, one can easily predetermine the items and patterns of the measurement and the variation of temperature. According to this invention, the apparatus 100 is capable of not only measuring the internal friction behavior, expansion and/or the magnetic property change of the metal specimen during the heating, cooling and isothermal heating proceedings of the heat treatment, but also capable of keeping the specimen 31 in-situ while conduting those measuements. Thus, the apparatus provides a considerable amount of valuable measured data which can not be obtained with known skills and is significantly meaningful to the study of metals.

Figure 3:
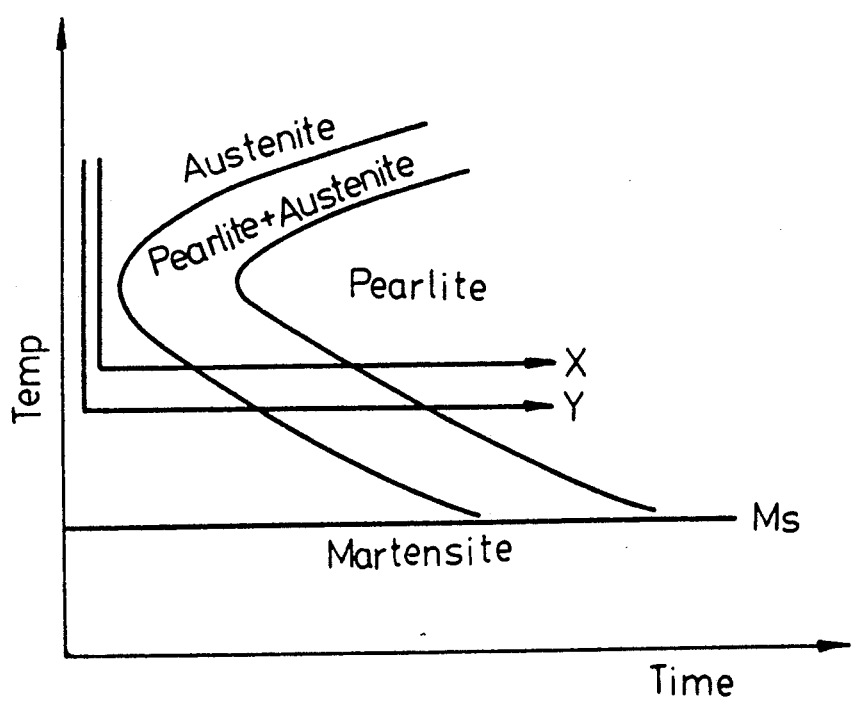
FIG. 3 is a chart of a time-temperature-transformation curve for illustrating the phase transformations of an iron-based alloy, in which lines X and Y are predetermined conditions, using the method of this invention to investigate the phase transformation for different periods with an isothermal in-situ measurement procedure.

As an example, FIG. 3 shows a time-temperature-transformation curve of an iron-based alloy during heat treatment which illustrates the phase transformations of the alloy. By using the traditional apparatus, a skilled person may obtain the results of the phase transformations shown in FIG. 3.

However, various information cannot be obtained from the results. For instance, when the crystal structure of the iron-based alloy transform from the austenite phase into the pearlite phase, persons skilled in the art find it difficult to get information during transformation process, especially, during such period of the incubation.

It is clearly shown in FIG. 3 that lines X and Y represent respectively, a specimen of an iron-based alloy cooled radily from a higher temperature to a lower temperature and then kept in an isothermal proceeding for a certain period. By using the apparatus of this invention disclosed previously, the detailed measurements of the internal friction of the iron-based alloy can be obtained not only in the situation of a single phase but also in process of phase transformation, such as the austenite range to the range of austenite and perlite, and then eventually to perlite range. In other words, according to this invention, after changes of the magnetic flux and/or expansion curve are measured, one will know that the phase transformation has been effected. Therefore, the obtained values of the internal friction of the alloy before, during, and after the phase transformations will be significantly useful for the further study of metal.

It should be understood that any person skilled in the art may make some minor modifications in light of the previous description of this invention. However, such modifications shall fall into the scope of the appended claims.

What is claimed is:

1. An apparatus for determining in-situ an internal friction of a metal specimen comprising: a vacuum housing means for mounting a metal specimen in said vacuum housing, said mounting means having means for fixing one end of said metal specimen, a fulcrumed lever provided above said fixing means, means for hanging the other end of said metal specimen on one end of said lever, and a weighing member attached to the other end of said lever; an internal friction measuring means; means for heating said metal specimen at a controlled heating rate; means for cooling said metal specimen at a controlled cooling rate; means for measuring the temperature of said metal specimen; an electromagnetic dialometer connected to said weighing member for determining the thermal expansion of said metal specimen; means for determining the varying internal friction of said metal specimen; and a control means connected to said temperature measuring means, said heating means, said cooling means and said internal friction measuring means for controlling the temperature of said metal specimen and for controlling said internal friction measuring means to determine varying values of the internal friction at certain controlled temperatures; and means for recording the varying thermal expansion of said metal specimen connected to said electromagnetic dialometer.

2. An apparatus as claimed in claim 1, further comprising means for determining the magnetic properties of said metal specimen at said certain controlled temperatures, said magnetic property determining means connected to said control means.

* * * * *